United States Patent [19]
Matsumoto et al.

[11] Patent Number: 5,089,404
[45] Date of Patent: Feb. 18, 1992

[54] PROCESS FOR THE TRANSESTERIFICATION OF FAT AND OIL

[75] Inventors: Wataru Matsumoto; Eiji Nakai, both of Tokyo; Toru Nezu, Chiba; Kazuaki Suzuki, Nishi, all of Japan

[73] Assignee: The Japanese Research and Development Association for Bioreactor System in Food Industry, Tokyo, Japan

[21] Appl. No.: 261,162

[22] Filed: Oct. 21, 1988

[30] Foreign Application Priority Data

Dec. 22, 1987 [JP] Japan .................. 62-324559

[51] Int. Cl.$^5$ .................................. C12P 7/64
[52] U.S. Cl. ........................ 435/134; 435/939; 435/921; 435/931; 435/829; 435/822
[58] Field of Search .............. 435/134; 426/33, 52, 426/607

[56] References Cited

U.S. PATENT DOCUMENTS

4,275,081 6/1981 Coleman et al. ............ 435/134 X
4,735,900 4/1988 Urata et al. ................. 435/134
4,940,845 7/1990 Hirohita et al. ............. 435/134

FOREIGN PATENT DOCUMENTS

126416 11/1984 European Pat. Off. ......... 435/134
274798 7/1988 European Pat. Off. .
60-78587 5/1985 Japan ........................ 435/134
60-234590 11/1985 Japan ........................ 435/134
2188057 9/1987 United Kingdom .......... 435/134

OTHER PUBLICATIONS

Lazar et al., In: World Conference of Emerging Technol. Fats, Oils, Ind. (1985) pp. 346–354.

Primary Examiner—Carolyn Elmore
Attorney, Agent, or Firm—Frishauf, Holtz, Goodman & Woodward

[57] ABSTRACT

A process for the transesterification of substrates comprising (a) fat and oil and (b) one or more compounds selected from the group consisting of fatty acid, fatty acid ester and other fat and oil with the use of a lipase, wherein said transesterification is effected in the presence of a monohydric lower alcohol.

16 Claims, No Drawings

PROCESS FOR THE TRANSESTERIFICATION OF FAT AND OIL

BACKGROUND OF THE INVENTION

1. Field of the Invention

This invention relates to a process for the transesterification of fat and oil. More particularly, it relates to a process for the transesterification of fat and oil by using a lipase whereby a transesterified fat and oil of high quality can be readily obtained.

2. Description of the Prior Art

Conventional processes for the transesterification of fats comprise employing various catalysts such as alkali metals and alkali matal alcholates. However none of these processes shows the specificity of the site at which the traansesterification occurs. Thus recently it has been attempted to effect site-specific transesterification by using a lipase.

In order to effect transesterification by using a lipase as a catalyst, it is required to control the moisture content in the reaction system. When the moisture content in the reaction system is too low, the lipase cannot be sufficiently activated and thus the aimed reaction cannot be achieved. When the moisture content is excessively high, on the other hand, the fat is hydrolyzed, which would cause, for example, a decrease in the yield of triglycerides or the deterioration of the obtained transesterified fat. Therefore transesterification with the use of a lipase should be effected under strict control of the moisture content. However water is hardly soluble in substrates or in an organic solvent and the range of the moisture content effective in the reaction is narrow, which makes the control of the moisture content difficult.

SUMMARY OF THE INVENTION

It is an object of the present invention to provide a process for the transesterification of fat and oil by using a lipase whereby a transestrified fat and oil of high quality can be readily obtained.

This object of the present invention has been achieved by providing a process for transesterifying substrates comprising (a) fat and oil and (b) one or more compounds selected from the group consisting of fatty acid, fatty acid ester and other fat and oil, by using a lipase, wherein said transesterification is effected in the presence of a monohydric lower alcohol.

DETAILED DESCRIPTION OF THE INVENTION

The fat and oil to be used in the present invention or other fat and oil to be transesterified therewith are not particularly restricted, and any edible animal and/or vegetable fat and oil commonly used may be employed therefor. Examples thereof include palm oil, rapeseed oil, sunflower oil, safflower oil, shea fat, salt fat, chinese tallow, fish oil, beef tallow and lard which are optionally fractionated or hardened, and they are used alone or as a mixture thereof.

The fatty acids to be used in the present invention include saturated and/or unsaturated fatty acids carrying 8 to 22 carbon atoms which are normally found in the natural world, such as palmitic acid, stearic acid, arachic acid, behenic acid, oleic acid and linoleic acid.

The fatty acid esters to be used in the present invention include lower alcohol esters of the above fatty acids. Preferably examples thereof include esters of mono- or higher-hydric alcohols carrying one to three carbon atoms with the above fatty acids, such as glycerol monofatty acid esters, glycerol difatty acid esters, propylene glycol fatty acid esters and methyl oleate, though it is not restricted thererto.

The lipase to be used in the present invention is not particularly restricted but any known one may be optionally selected.

The lipase may have a selectivity for, e.g., a substrate or site or a lipase which does not have any selectivity may also be employable. Examples of a lipase having a specificity at the 1,3-position of glyceride include those originating from microorganisms belonging to the genera Rhizopus, Mucor and Alcaligenes and pancreatic lipase. Examples of a lipase having no selectivity include those originating from microorganisms belonging to the genera Chromobacterium and Candida.

Although these lipases may be used as such, it is preferable to immobilize the same on a carrier such as Celite, an ion exchange resin or chitosan. Any carrier may be selected therefor without limitation, so long as it would not inhibit the activity of the lipase.

Preferable examples of the monohydric lower alcohol to be used in the present invention are those having four or less carbon atoms such as methanol, ethanol, propranol, isopropanol and butanol. Among these alcohols, ethanol is particularly preferable.

The process of the present invention relates to transesterification of substrates comprising (a)fat and oil and (b) one or more compounds selected from the group consisting of fatty acid, fatty acid ester and other fat and oil with a lipase, wherein the transesterification is effected in the presence of a monohydric lower alcohol. It is preferable to add said monohydric lower alcohol in an amount of 0.03% by weight or above, based on the substrates, still preferably 0.03 to 4.0% by weight, still preferably 0.1 to 4.0% by weight and most preferably 0.1 to 2.0% by weight.

An amount of the monohydric lower alcohol less than 0.03% by weight would cause a low transesterification ratio. When it exceeds the above range, on the other hand, undesirable hydrolysis might proceed.

In the process of the present invention, it is preferable to minimize the moisture in the reaction system, since the moisture would cause hydrolysis of the fat and oil to thereby accelerate the formation of side-products such as diglycerides(s), which lowers the yield of the triglycerides(s). It is desirable to lower the moisture content to 0.18% by weight or below, based on the substrate, still preferably to 0.15% by weight or below. However it costs a great deal to completely remove the moisture. Further it requires complicated procedures. Thus from a practical viewpoint, it is desirable to lower the moisture content to 0.01 to 0.15% by weight, still preferably to 0.02 to 0.1% by weight.

In the embodiment of the present invention, if necessary, an organic solvent such as hexane or acetone may be added to the reaction system.

As reaction conditions for putting the present invention into practice, it is sufficient if temperature and period may be appropriately selected depending on the aimed product and the enzyme to be used. Generally the reaction may be effected at a temperature of 20° to 80° C. When the reaction is effected batchwise, the reaction period may range from 1 to 72 hours. When it is continuously effected, the reaction period may range one minute to one hour.

The transesterification process of the present invention is effected under the conditions as specified above and then the reaction product is purified by, for example, distillation, liquid/liquid extraction or solvent fractionation. Thus the aimed transesterified fat and oil may be readily obtained.

The present invention will further be illustrated by reference to the following examples, however, they are not to be construed to limit the scope of the invention.

EXAMPLE 1

To 30 g of palm oil medium fraction were added 24 g of stearic acid and 120 g of n-hexane. Then 0.3% by weight, 0.6% by weight, 1.2% by weight and 2.0% by weight, each based on the substrates, of ethanol were added thereto. Each mixture thus obtained was thoroughly dehydrated with Molecular Sieve 3A to thereby give a moisture content of 0.02% by weight based on the substrate. Then 2 g of an immobilized lipase was added thereto and the resulting mixture was reacted at 40° C. under stirring for 24 hours. The reaction product thus obtained was trimethylsilylated with the use of hexamethyldisilazane (HMDS) and trimethylchlorosilane (TMC) (mfd. Wako Pure Chemical Industries, Ltd.) according to a process reported by J. Blum et al. (cf. Lipid, 5, 601 (1970)) and the composition of the product was analyzed by gas chromatography. The immobilized lipase as described above was prepared according to a process described in Japanese Patent Laid-Open No. 213390/1984. Namely, 5.15 g of Rhizopus dekenar lipase (mfd. by Seikagaku Kogyo K. K., originating from Rhizopus) was immobilized through adsorption on 100 g of a composite carrier comprising chitosan and Celite.

For comparison, the same procedure as above was repeated except that no ethanol was added (moisture content based on the substrates: 0.02% by weight) and that the ethanol was replaced with 0.2% by weight of water, based on the substrates. Table 1 shows the results.

Table 1 obviously indicates that the addition of ethanol would elevate the efficiency of the transesterification. That is to say, when ethanol was added, the triglyceride carrying 50 carbon atoms was decreased while those carrying 52 and 54 carbon atoms were increased, compared with the starting fat.

In contrast thereto, when no ethanol was added, the reaction hardly proceeded. When no ethanol was added but 0.2% by weight of water was added, the obtained product contained a large amount of diglycerides and was poor in the quality.

TABLE 1

|  | C50 | C52 | C54 | Others | DG content |
|---|---|---|---|---|---|
| Starting fat | 69.5 | 21.3 | 3.9 | 5.3 | 3.3 |
| Ex. ethanol (%) | | | | | |
| 0.3 | 27.5 | 46.0 | 23.9 | 2.6 | 6.5 |
| 0.6 | 19.5 | 46.8 | 31.5 | 2.2 | 8.0 |
| 1.2 | 19.8 | 46.2 | 32.1 | 1.8 | 9.3 |
| 2.0 | 19.7 | 46.5 | 32.2 | 1.6 | 14.5 |
| Comp. Ex. | | | | | |
| none | 33.0 | 46.4 | 16.9 | 3.7 | 4.1 |
| water (0.2%) | 17.5 | 44.2 | 31.5 | 6.8 | 17.5 |

Note:
In the above Table 1, DG content shows the content (% by weight) of diglycerides in the product. C50 to 54 and others show the contents (% by weight) of triglycerides carrying 50 to 54 carbon atoms and other triglycerides in the total triglycerides respectively.

EXAMPLE 2

One part by weight of palm oil, 0.8 part by weight of stearic acid and 4.5 parts by weight of hexane were thoroughly dehydrated with Molecular Sieve 3A. 0.01 part by weight of ethanol or 0.007 part by weight of methanol was added thereto. Each mixture thus obtained was fed into a column (0.9 cm (diameter)×6 cm (height)) containing 2 g of an immobilized lipase at a flow rate of 18 ml/hr and thus reacted at 45° C. The reaction product thus obtained was eluted stepwise by column chromatography (carrier: silica gel, developing solvent: n-hexane and n-hexane/ether=70/30) to thereby collect the triglyceride fraction. A sample of this fraction was methylesterified to thereby determine the content of the stearic acid incorporated into the triglycerides. The immobilized lipase used above was prepared by blending five parts by weight of Duolite S587, one part by weight of Rhizopus delemar (disclosed in Japanese Patent Laid-Open No. 289884/1986) and ten parts by weight of a 0.1M phosphate buffer solution (pH 7.0), the resulting mixture was allowed to stand for ten hours and then dried.

For comparison, the same procedure as above was repeated except that the ethanol or methanol was replaced with 0.15% by weight of water, based on the substrates. Table 2 shows the results.

TABLE 2

| Reaction period (day) | Stearic acid contained in triglycerides produced (% by weight) | | |
|---|---|---|---|
| | Example | | Comp. Example |
| | ethanol | methanol | water |
| 1 | 38.9 | 38.5 | 36.8 |
| 4 | 38.6 | 38.4 | 33.5 |
| 10 | 37.7 | 38.0 | 30.5 |

The content of stearic acid in the starting oil was 4.2% by weight

EXAMPLE 3

The same procedure as Example 1 was repeated except that the moisture content in the reaction system was adjusted to 0.1% by weight based on the substrates and that the ethanol content was adjusted to 0.1% by weight, 0.3% by weight, 0.6% by weight and 1.2% by weight, each based on the substrates.

For comparison, the same procedure as above was repeated except that no ethanol was added (moisture content: 0.1% by weight based on the substrates). Table 3 shows the results.

TABLE 3

|  | C50 | C52 | C54 | Others | DG content |
|---|---|---|---|---|---|
| Starting fat | 69.5 | 21.3 | 3.9 | 5.3 | 3.3 |
| Ex. ethanol (%) | | | | | |
| 0.1 | 26.5 | 46.3 | 24.8 | 2.7 | 8.5 |
| 0.3 | 22.9 | 46.5 | 28.2 | 2.4 | 9.0 |
| 0.6 | 19.5 | 46.7 | 31.7 | 2.1 | 12.1 |
| 1.2 | 19.9 | 46.4 | 32.0 | 1.7 | 14.8 |
| *none | 29.5 | 46.2 | 20.3 | 4.0 | 6.2 |

Note:
*Comparative Example.
The DG content. C50 to 54 and others are as defined above.

EXAMPLE 4

One part by weight of sunflower oil and one part by weight of stearic acid were thoroughly dehydrated with Molecular Sieve 3A and then 0.01 part by weight of ethanol was added thereto. The resulting mixture was fed to columns (9 cm (diameter)×18 cm (height)) each containing 3 g of LYPOZYM (mfd. by Novo Co., lipase originating from Mucor) at flow rates of 12 ml/hr and 6 ml/hr respectively and thus reacted at 69° C. Each product thus obtained was analyzed in the same manner as the one described in Example 2.

For comparison, the same procedure as above was repeated except that the ethanol was replaced with an excessive amount of water, i.e., the substrates were saturated with water. Table 4 shows the results.

TABLE 4

|  | Incorporated stearic acid (% by weight) | |
| --- | --- | --- |
|  | 6 ml/hr | 12 ml/hr |
| Example 4 | 42.0 | 32.9 |
| Comp. Ex. | 39.1 | 27.2 |

The starting material contained 3.7% by weight of stearic acid.

EXAMPLE 5

30 g of palm oil and 70 g of rapeseed oil were thoroughly dehydrated with Molecular Sieve 3A and then 1 g of ethanol and 3 g of an immobilized lipase were added thereto. The resulting mixture was extracted at 69° C. for 24 hours under stirring. The above immobilized lipase was prepared in the same manner as the one described in Example 1. Namely, 3 g of a lipase originating from *Candida cylindrasse* (LIPASE OF: mfd. by Meito Sangyo Co., Ltd.) was immobilized through adsorption on 100 g of a composite carrier comprising chitosan and Celite. Then the triglyceride composition (% by weight) and SFC (solid fat content) were determined. The latter was determined according to a conventional method specified in American Oil Chemical Society Recommended Pracice Cd16-18 Solid Fat Content with the use of PRAXIS MODEL SFC-900. Table 5 shows the results.

TABLE 5

|  | Starting material | Reaction product |
| --- | --- | --- |
| m.p. (°C.) | 26.4 | 15.7 |
| Diglyceride content (% by weight) | 3.0 | 6.0 |
| Triglyceride content (% by weight) |  |  |
| Carbon atom No. |  |  |
| 46 | 0.7 | 0.5 |
| 48 | 3.7 | 2.7 |
| 50 | 14.1 | 10.5 |
| 52 | 20.9 | 34.2 |
| 54 | 52.3 | 46.6 |
| 56 | 3.8 | 3.3 |
| 58 | 1.4 | 1.4 |
| 60 | 0.4 | 0.3 |
| SFC |  |  |
| 1° C. | 11.4 | 8.9 |
| 10 | 9.4 | 4.9 |
| 20 | 4.3 | 1.5 |
| 25 | 2.4 | 0.1 |
| 30 | 2.0 | — |
| 33 | 1.5 | — |
| 35 | 1.3 | — |

What is claimed is:

1. A process for producing a triglyceride by the transesterification of a substrate, said substrate comprising (a) a first fat or oil and (b) one or more compounds selected from the group consisting of a fatty acid, a fatty acid ester and a second fat or oil, the process comprising contacting said substrate with a lipase in the presence of 0.1% by weight to 2% by weight of ethanol, based on the substrate and the moisture content in the resultant reaction system is from 0% by weight to 0.18% by weight, based on the substrate.

2. The transesterification process as set forth in claim 1, wherein the moisture content in the reaction system is from 0.01% by weight to 0.15% by weight, based on the substrate.

3. The process as set forth in claim 1, wherein the substrate comprises a fat or oil selected from the group consisting of palm oil, rapeseed oil, sunflower oil, safflower oil, shea fat, salt fat, chinese tallow, fish oil, beef tallow and lard.

4. The process as set forth in claim 1, wherein the substrate comprises a fatty acid selected from the group consisting of palmitic acid, stearic acid, arachic acid, behenic acid, oleic acid and linoleic acid.

5. The process as set forth in claim 1, wherein the substrate comprises a fatty acid ester selected from the group consisting of glycerol monofatty acid esters, glycerol difatty acid esters, propylene glycol fatty acid esters and methyl oleate.

6. The process as set forth in claim 1, wherein the lipase is a lipase originating from a microorganism selected from the group consisting of Rhizopus, Mucor, Alcaligenes, Chromobacterium and Candida.

7. The process as set forth in claim 1, wherein the lipase is *Rhizopus dekenar* lipase or *Rhizopus delemar* lipase.

8. The process as set forth in claim 1, wherein the lipase is a lipase originating from *Candida cylindrase*.

9. The process as set forth in claim 1, wherein the transesterification is conducted at a temperature of 20° to 80° C. for a period of 1 to 72 hours.

10. The process as set forth in claim 2, wherein the substrate comprises palm oil and stearic acid and the lipase is *Rhizopus dekenar* lipase or *Rhizopuss delemar* lipase.

11. The process as set forth in claim 1, wherein the substrate comprises sunflower oil and stearic acid and the lipase originates from Mucor.

12. The process as set forth in claim 2, wherein the substrate comprises palm oil and rapeseed oil and the lipase originates from *Candida cylindrasse*.

13. The process as set forth in claim 2, wherein the transesterification is conducted at a temperature of 20° to 80° C. for a period of 1 to 7 hours.

14. The process as set forth in claim 10, wherein the transesterification is conducted at a temperature of 20° to 80° C. for a period of 1 to 7 hours.

15. The process as set forth in claim 11, wherein the transesterification is conducted at a temperature of 20° to 80° C. for a period of 1 to 7 hours.

16. The process as set forth in claim 12, wherein the transesterification is conducted at a temperature of 20° to 80° C. for a period of 1 to 7 hours.

* * * * *